United States Patent
Hammond et al.

(10) Patent No.: US 8,004,672 B2
(45) Date of Patent: Aug. 23, 2011

(54) CLOSED CELL FOR USE IN SPECTROPHOTOMETERS

(75) Inventors: John Hammond, Essex (GB); Keith Hume, Essex (GB)

(73) Assignee: Starna Scientific Limited (GB)

( * ) Notice: Subject to any disclaimer, the term of this patent is extended or adjusted under 35 U.S.C. 154(b) by 21 days.

(21) Appl. No.: 12/443,287

(22) PCT Filed: Oct. 11, 2007

(86) PCT No.: PCT/GB2007/003874
§ 371 (c)(1),
(2), (4) Date: Mar. 27, 2009

(87) PCT Pub. No.: WO2008/044037
PCT Pub. Date: Apr. 17, 2008

(65) Prior Publication Data
US 2010/0073673 A1  Mar. 25, 2010

(30) Foreign Application Priority Data
Oct. 12, 2006  (GB) ................................. 0620265.9

(51) Int. Cl.
*G01N 1/10* (2006.01)

(52) U.S. Cl. .......................... 356/246; 356/440; 250/373
(58) Field of Classification Search ................... 356/246, 356/244; 422/82
See application file for complete search history.

(56) References Cited

U.S. PATENT DOCUMENTS

| | | | | |
|---|---|---|---|---|
| 3,508,837 A | * | 4/1970 | Hrdina | 356/246 |
| 3,795,451 A | * | 3/1974 | Mailen | 356/246 |
| 3,867,042 A | * | 2/1975 | Mayer et al. | 356/246 |
| 4,565,446 A | * | 1/1986 | Chu | 356/246 |
| 5,475,486 A | * | 12/1995 | Paoli | 356/246 |
| 5,831,727 A | * | 11/1998 | Stream | 356/246 |
| 2005/0168737 A1 | * | 8/2005 | Bradshaw et al. | 356/319 |
| 2006/0073609 A1 | * | 4/2006 | Shimizu | 436/180 |

* cited by examiner

*Primary Examiner* — Tarifur Chowdhury
*Assistant Examiner* — Michael LaPage
(74) *Attorney, Agent, or Firm* — Stites & Harbison, PLLC; David W. Nagle, Jr.; Stephen J. Weyer

(57) ABSTRACT

A closed cell for use in spectrophotometers is adapted to receive a liquid to be subjected to analysis and an air space or bubble to absorb pressure differentials, wherein the cell includes means to retain the air space or bubble in a predetermined location in the cell.

6 Claims, 2 Drawing Sheets

CLOSED CELL FOR USE IN SPECTROPHOTOMETERS

FIELD OF THE INVENTION

The present invention relates to a closed cell, particularly but not exclusively, a cell used in analytical equipment such as a spectrophotometer.

BACKGROUND OF THE INVENTION

Analytical equipment such as spectrophotometers are routinely used in the quantitative determination of the concentration of solutions of transition metal ions and highly conjugated organic compounds. The concentration of such solutions may be determined by measuring the absorbance of light passing through a sample of the solution. In such analysis, light, often ultra violet (UV), is passed through the sample and a diffraction grating or monochromator is used to separate the different wavelengths, which are then detected by a photodiode or charged-coupled device (CCD).

To calibrate the spectrophotometer, a reference solution is used of a known concentration. Samples under analysis as well as reference solutions are contained in a cell or cuvette formed typically of a transparent material such as plastic, optical glass, Pyrex, UV Silica or quartz. These cells or cuvettes are typically formed as a square or round tube sealed at one end. Sample and reference solutions may also be contained in a cell sealed at both ends to prevent contamination. An air space or bubble is left in the cells containing a sample or reference solution so as to reduce the likelihood that, should the solution inside the cell expand with increased ambient temperature, the risk of the cell bursting is reduced.

Sample and reference cells are conventionally used in a vertical alignment. When cells are aligned vertically, the air space or bubble will rise to the top of the cell and will not impede the transmission of light during analysis of the sample. Some cells however may be used in a horizontal alignment such as those used with a so called Plate Reader. When the cells are aligned horizontally, the air bubble may become dispersed throughout the solution and thereby affect the transmission of light through the sample and consequently the test measurement. The present invention seeks to overcome the aforementioned problems.

BRIEF SUMMARY OF THE INVENTION

According to the present invention there is provided a closed cell for use in analytical equipment, adapted to receive a liquid to be subjected to analysis with an air space or bubble to absorb pressure differentials, wherein the cell includes means to retain the air space or bubble in a predetermined location in the cell. The means comprises a restriction element formed in a passage connecting a first chamber and a second chamber. The restriction element is adapted to facilitate the air space or bubble passing from the first to the second chamber and to inhibit the air space or bubble passing from the second chamber to the first chamber. The restriction element is formed by a transverse wall. The transverse wall extends partially across the first chamber to define a passage between a wall of the first chamber and the free end of the transverse wall. The free end of the transverse wall is profiled such that the area of the passage decreases in a direction from the first to the second chamber.

The means provided in the cell seeks to reduce the likelihood that air contained in second chamber flows unimpeded into the first chamber.

Preferably the cell comprises a first chamber fluidly connected to a second chamber, wherein the means to retain the air space or bubble comprises a restriction element formed in a passage connecting the first chamber and the second chamber and adapted to facilitate the air space or bubble passing from the first to the second chamber and to inhibit the air space or bubble passing from the second chamber to the first chamber.

Preferably the restriction element is formed by a transverse wall that extends partially across the chamber to define a passage between a wall of the first chamber and the free end of the transverse wall.

Preferably, the free end of the transverse wall is profiled such that the area of the passage decreases in a direction from the first to the second chamber.

Preferably, the second chamber provides a volume raised above that of the first chamber when the cell is in a horizontal position further reducing the potential for the bubble to move back to the passage and into the first chamber.

Preferably, the cell includes an opening for filling the cell with liquid, the opening being sealable after the cell has been filled with liquid.

Preferably the cell is formed of plastic, optical glass, Pyrex, UV Silica or quartz.

BRIEF DESCRIPTION OF THE DRAWINGS

A preferred embodiment of the present invention shall now be described by way of example by reference to the following drawings in which.

DETAILED DESCRIPTION OF THE INVENTION

Figure 1:
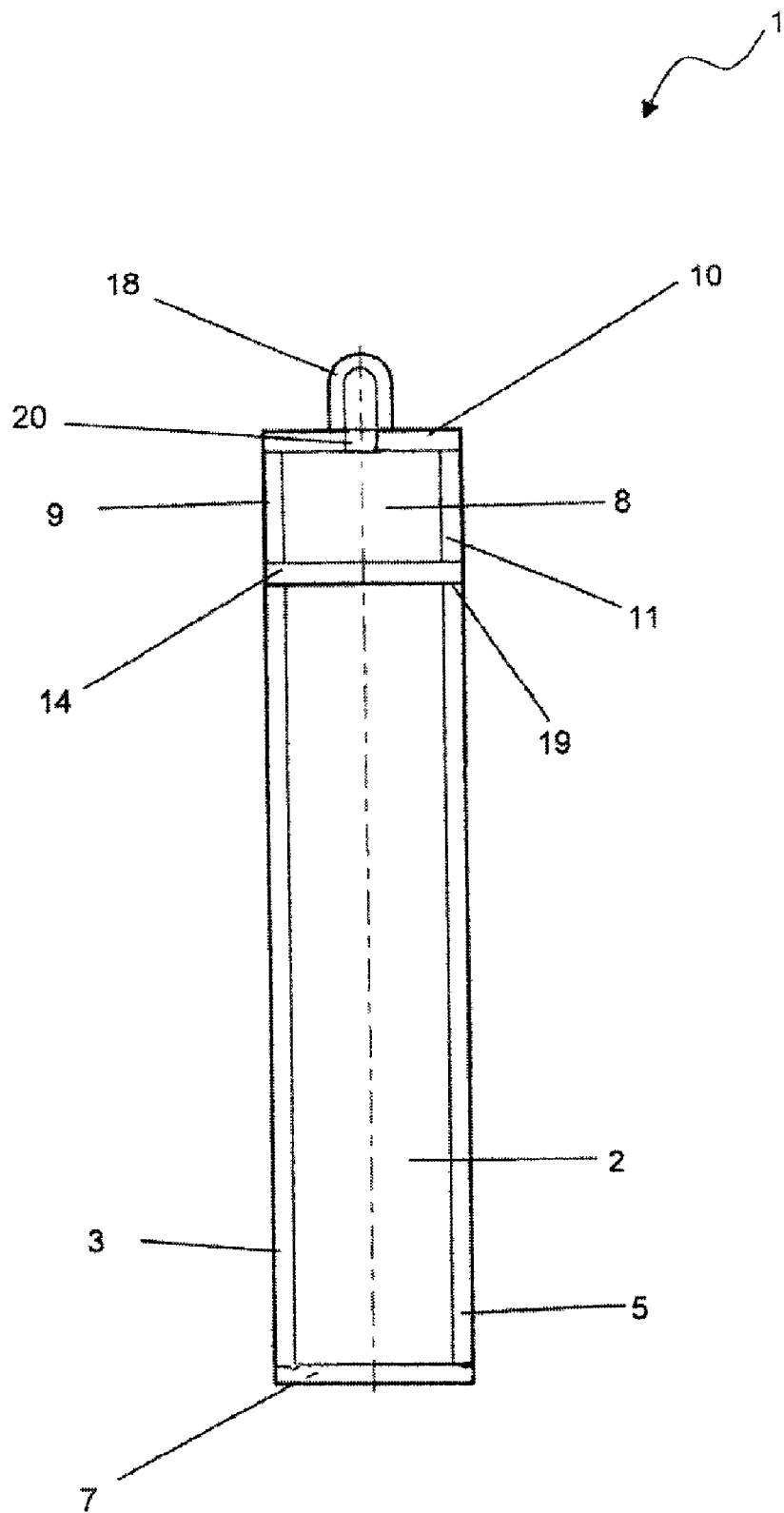
FIG. 1 shows a front projection of a preferred embodiment of the present invention.
Figure 2:
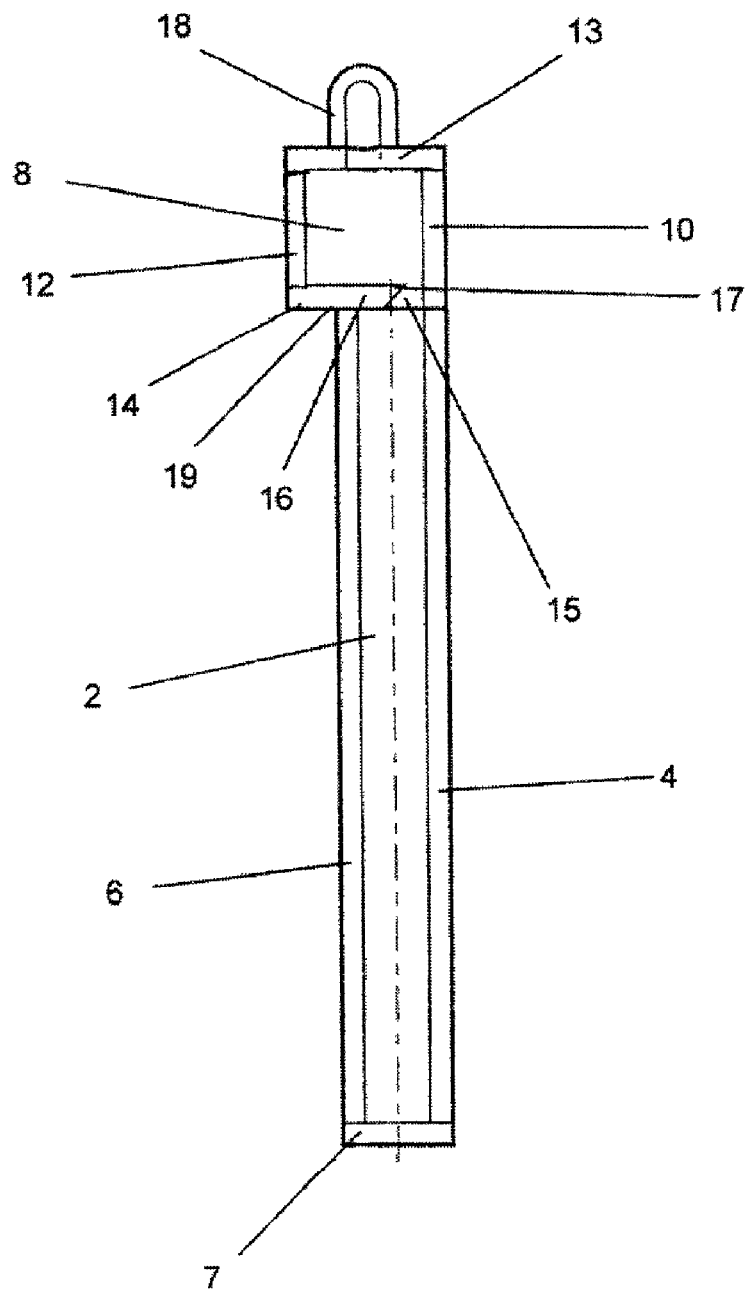
FIG. 2 shows a cross section through a side projection of the embodiment shown in FIG. 1.

A closed cell shown generally as 1 comprises a first chamber 2 formed of a first, second, third and fourth planar rectangular side walls 3, 4, 5, 6 adjoining at their shorter edges to a planar rectangular base 7 to form a substantially cuboid chamber open at one end. The cell 1 further comprises a second chamber 8 comprising a fifth, sixth, seventh and eighth planar rectangular side walls 9, 10, 11, 12, and a planar rectangular lid 13 to form a substantially cuboid chamber 8 open at one end.

At the open end of the second chamber 8, the edges of the fifth, sixth and seventh side walls 9, 10, 11 are aligned with the edges of the first, second and third side walls 3, 4, 5 respectively at the open end of the first chamber 2. The fifth, sixth and seventh side walls 9, 10, 11 are thus aligned in the same planes as the first, second and third side walls 3, 4, 5 respectively.

The eighth side wall 12 of the second chamber 8 is offset from the plane of the fourth side wall 6 of the first chamber 2. The second chamber 8 comprises a substantially planar rectangular base 14 by which the edge of the eighth side wall 12 of the second chamber 8 is joined to the fourth side wall 6 of the first chamber 2 to close the open end at a connecting section 19. The second chamber 8 thereby overhangs the first chamber 2 to provide a volume positioned above the second side wall 6 when the cell is positioned with the second side wall 4 lowermost and resting substantially horizontally when installed on a plate reader.

The first chamber 2 is fluidly connected to the second chamber 8 via a fluid passage 15. A restriction element 16 is formed by a transverse planar wall 16 which is integrally formed with the base 14 of the second chamber 8 and extends partially across the first chamber 2 at the connecting section 19 to define the passage 15 between the free edge of the transverse wall 16 and the inner surface of the second planar wall 4. The extended free edge of the transverse planar wall 16 is inclined at an angle 17 such that the area of the passage 15 decreases in the direction from the first chamber 2 to the second chamber 8.

The planar rectangular lid 13 of the second chamber 8 is provided with an opening 20 to which an open-ended tube 18 is secured. This opening enables the cell to be filled through the tube with a sample solution or liquid. After filling the cell completely, apart from a small air bubble, the open end of the tube 18 over the opening 20 in the second chamber 8 is sealed.

The liquid contained in the cell may expand with increased temperature. The air space or bubble is provided to reduce the likelihood that the cell should break as the air space or bubble is more easily compressed and absorbs the pressure differential which results from the volumetric expansion of the liquid.

As the cell is moved, for example during general handling, air may flow from the air space into the first chamber 2 and then, when the cell 1 is aligned in a horizontal position, such that the second planar rectangular side wall 4 lies horizontally and lowermost such as during testing, air may remain in the first chamber 2 and affect accuracy of the measurement of the concentration of the solution. To eliminate the air in the first chamber 2, the cell is first aligned in a vertical position with the second chamber 8 uppermost to allow the air to flow from the first chamber 2 through the passage 15 into the second chamber 8. When the tube 1 is re-aligned in a horizontal position with the second wall 4 lowermost, the restriction element 16 of the second chamber 8 serves to reduce the likelihood that air may flow back into the first chamber 2. In addition the raised volume of the second chamber 8, when the cell is aligned with the second side wall 4 lowermost resting substantially horizontally, further reduces the potential for the air bubble to move down to the passage 15 and hence into the first chamber 2 therefore improves the efficiency of the cell in preventing air returning to the first chamber 2.

Although described as an air bubble, it will be understood that other gases may be used such as nitrogen or an inert gas such as helium.

The cell 1 may be formed as one piece from a transparent material such as plastic, optical glass, Pyrex, UV Silica or quartz. Depending upon the application of the sample cell, one or more of the rectangular planar side walls 3, 4, 5, 6, 9, 10, 11, 12 may be opaque.

The invention claimed is:

1. A device for use in analytical equipment, adapted to receive a liquid to be subjected to analysis with an air space or bubble to absorb pressure differentials, the device comprising:
a closed cell having means to retain the air space or bubble in a predetermined location in the closed cell, the means comprising a restriction element formed in a passage connecting a first chamber and a second chamber and adapted to facilitate the air space or bubble passing from the first chamber to the second chamber and to inhibit the air space or bubble passing from the second chamber to the first chamber, the restriction element being formed by a transverse wall, which transverse wall extends partially across the first chamber to define a passage between a wall of the first chamber and the free end of the transverse wall and wherein, the free end of the transverse wall is profiled such that the area of the passage decreases in a direction from the first to the second chamber.

2. The device according to claim 1, wherein the second chamber has a volume raised above that of the first chamber when the cell is in a horizontal position further reducing the potential for the bubble to move to the passage and into the first chamber.

3. The device according to claim 1, wherein the closed cell includes an opening for filling the cell with liquid, the opening being sealable after the cell has been filled with liquid.

4. The device according to claim 1, wherein the closed cell is formed of a transparent material.

5. The device according to claim 4, wherein the material is selected from the groups consisting of plastic, optical glass, Pyrex, UV Silica and quartz.

6. The device of claim 1, wherein the closed cell has a closed configuration which prevents fluids from entering or exiting.

* * * * *